United States Patent
Shechter (10) Patent No.: US 8,577,113 B2
(45) Date of Patent: Nov. 5, 2013

(54) IMAGE RECONSTRUCTION FOR TRUNCATED DETECTOR ARRAY

(75) Inventor: Gilad Shechter, Haifa (IL)

(73) Assignee: Koninklijke Philips N.V., Eindhoven (NL)

( * ) Notice: Subject to any disclaimer, the term of this patent is extended or adjusted under 35 U.S.C. 154(b) by 527 days.

(21) Appl. No.: 12/893,012

(22) Filed: Sep. 29, 2010

(65) Prior Publication Data

US 2011/0096971 A1    Apr. 28, 2011

Related U.S. Application Data

(60) Provisional application No. 61/253,884, filed on Oct. 22, 2009.

(51) Int. Cl.
*G06K 9/00* (2006.01)

(52) U.S. Cl.
USPC .................................. 382/131; 378/4; 378/21

(58) Field of Classification Search
None
See application file for complete search history.

(56) References Cited

U.S. PATENT DOCUMENTS

| | | | |
|---|---|---|---|
| 5,625,660 A * | 4/1997 | Tuy ................................. | 378/15 |
| 6,041,097 A | 3/2000 | Roos et al. | |
| 6,118,841 A | 9/2000 | Lai | |
| 7,113,570 B2 | 9/2006 | Toth et al. | |
| 2002/0196893 A1* | 12/2002 | Gordon ............................ | 378/4 |
| 2007/0071160 A1* | 3/2007 | Nishide et al. .................... | 378/4 |
| 2007/0110211 A1 | 5/2007 | Hsieh et al. | |
| 2009/0122955 A1* | 5/2009 | Bruder ............................. | 378/14 |
| 2010/0246752 A1* | 9/2010 | Heuscher et al. ................. | 378/4 |

OTHER PUBLICATIONS

Koken, P., et al.; Aperture weighted cardiac reconstruction for cone-beam CT; 2006; Phys. Med. Biol.; 51:3433-3448.
Shechter, G., et al.; The frequency split method for helical cone-beam reconstruction; 2004; Med. Phys.; 31(8) 2230-2236.
Zamyatin, A. A., et al.; Helical cone beam CT with an asymmetrical detector; 2005; Med. Phys.; 32(10)3117-3127.

* cited by examiner

*Primary Examiner* — Bhavesh Mehta
*Assistant Examiner* — Tahmina Ansari (57) ABSTRACT

A reconstruction system reconstructs projection data generated by a detector array of an imaging system having at least one truncated row of detector modules. The reconstruction system includes a projection data generator that augments the projection data with projection data created for the at least one truncated row of detector modules. The reconstruction system further includes a convolver that convolves the augmented projection data. The reconstruction system further includes a back-projector back-projects the augmented projection data and generates volumetric image data indicative thereof.

23 Claims, 6 Drawing Sheets

IMAGE RECONSTRUCTION FOR TRUNCATED DETECTOR ARRAY

CROSS REFERENCE TO RELATED APPLICATIONS

This application claims the benefit of U.S. provisional application Ser. No. 61/253,884 filed Oct. 22, 2009, which is incorporated herein by reference.

DESCRIPTION

The following generally relates to image reconstruction and finds particular application to computed tomography (CT). However, it also amenable to other medical imaging applications and to non-medical imaging applications.

A computed tomography (CT) scanner generally includes an x-ray tube mounted on a rotatable gantry that rotates around an examination region about a longitudinal or z-axis and emits radiation. An x-ray source collimator collimates the radiation to form a fan or cone-shaped radiation beam. A detector array subtends an angular arc opposite the examination region from the x-ray tube. The detector array detects radiation from the cone beam that traverses the examination region and a subject therein, and generates projection data indicative thereof. A reconstructor reconstructs the projection data and generates volumetric image data indicative of the scanned subject. Longitudinal wide-coverage cone beam CT allows for increasing scan time for helical scans and coverage (e.g., in cardiac and perfusion) for circular scans. A more recent trend is to manufacturer CT scanners with relatively small size detector pixels, which can help improve dose utility by reducing image noise for a fixed target spatial resolution.

Unfortunately, using small detector pixels can lead to a large number of relatively expensive detector pixels, which may increase the cost of the detector array. One approach to reducing this cost is to use larger detector pixels at the periphery of the detector array. However, this may increase the complexity of the mechanical design and serviceability. Another approach is to use a detector array that is asymmetric with respect to the gantry rotation center and fill in the missing projection rays by using rays belonging to a conjugate, or complementary, projection. Unfortunately, the cone angle of the direct and conjugate rays generally is different. With another approach, the inner rows of detector array cover the transverse extent, while the outer detector rows are transversally truncated. The inner rows can be used to compensate for the truncation artifacts caused by the outer rows. However, filling in the missing projections with the data from the inner rows longitudinally, followed by a row-by-row convolution with a ramp filter would result in unacceptable image artifacts.

Aspects of the present application address the above-referenced matters and others.

According to one aspect, a reconstruction system reconstructs projection data generated by a detector array of an imaging system having at least one truncated row of detector modules. The reconstruction system includes a projection data generator that augments the projection data with projection data created for the at least one truncated row of detector modules. The reconstruction system further includes a convolver that convolves the augmented projection data. The reconstruction system further includes a back-projector that back-projects the augmented projection data and generates volumetric image data indicative thereof.

In another embodiment, a method includes reconstructing wide-coverage cone-beam CT projection data generated by a detector array of an imaging system, wherein the detector array includes at least one truncated outer row of detector modules and at least one non-truncated inner row of detector modules.

In another embodiment, an imaging system includes a radiation source that rotates around and emits radiation that traverses an examination region and a source collimator including a set of dynamic collimators and a set of static collimators. The imaging system also includes a two dimensional truncated detector array having at least one truncated outer row of detector modules with an outer end region that does not include a detector module. The detector array generates projection data indicative of the radiation traversing the examination region.

The invention may take form in various components and arrangements of components, and in various steps and arrangements of steps. The drawings are only for purposes of illustrating the preferred embodiments and are not to be construed as limiting the invention.

Figure 1:
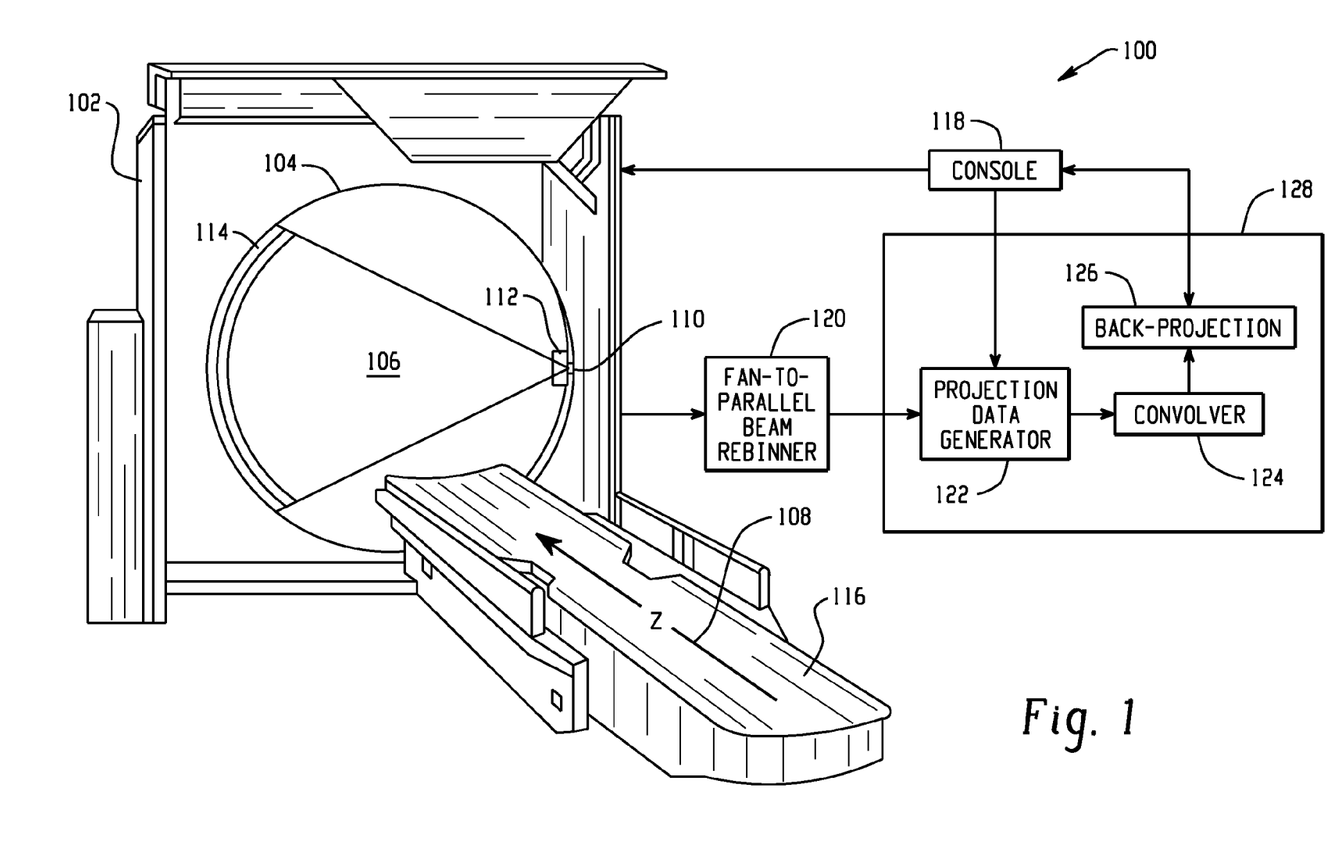
FIG. 1 illustrates an example imaging system.

FIG. 1 illustrates an imaging system 100 such as a compute tomography (CT) scanner. The imaging system 100 includes a stationary gantry 102 and a rotating gantry 104. The rotating gantry 104 is rotatably supported by the stationary gantry 102 and rotates around an examination region 106 about a longitudinal or z-axis 108.

A radiation source 110, such as an x-ray tube, is supported by the rotating gantry 104. The radiation source 110 emits radiation that traverses the examination region 106. A source collimator 112 collimates the emitted radiation to form a generally cone, fan, wedge, or otherwise shaped beam that traverses the examination region 106. As described in greater detail below, in one instance, the source collimator 112 includes a set of dynamic collimators for selectively defining a longitudinal beam opening (LBO) and a set of static collimators that attenuate or block radiation emitted towards missing detector modules that would otherwise irradiate the subject but not contribute to the reconstruction.

A radiation sensitive detector array 114 subtends an angular arc opposite the radiation sources 110 across the examination region 106. The detector array 114 detects radiation traversing the examination region 106 and the subject, and generates projection data indicative thereof. In one instance, the projection data corresponds to wide-coverage cone beam CT projection data.

Figure 2:
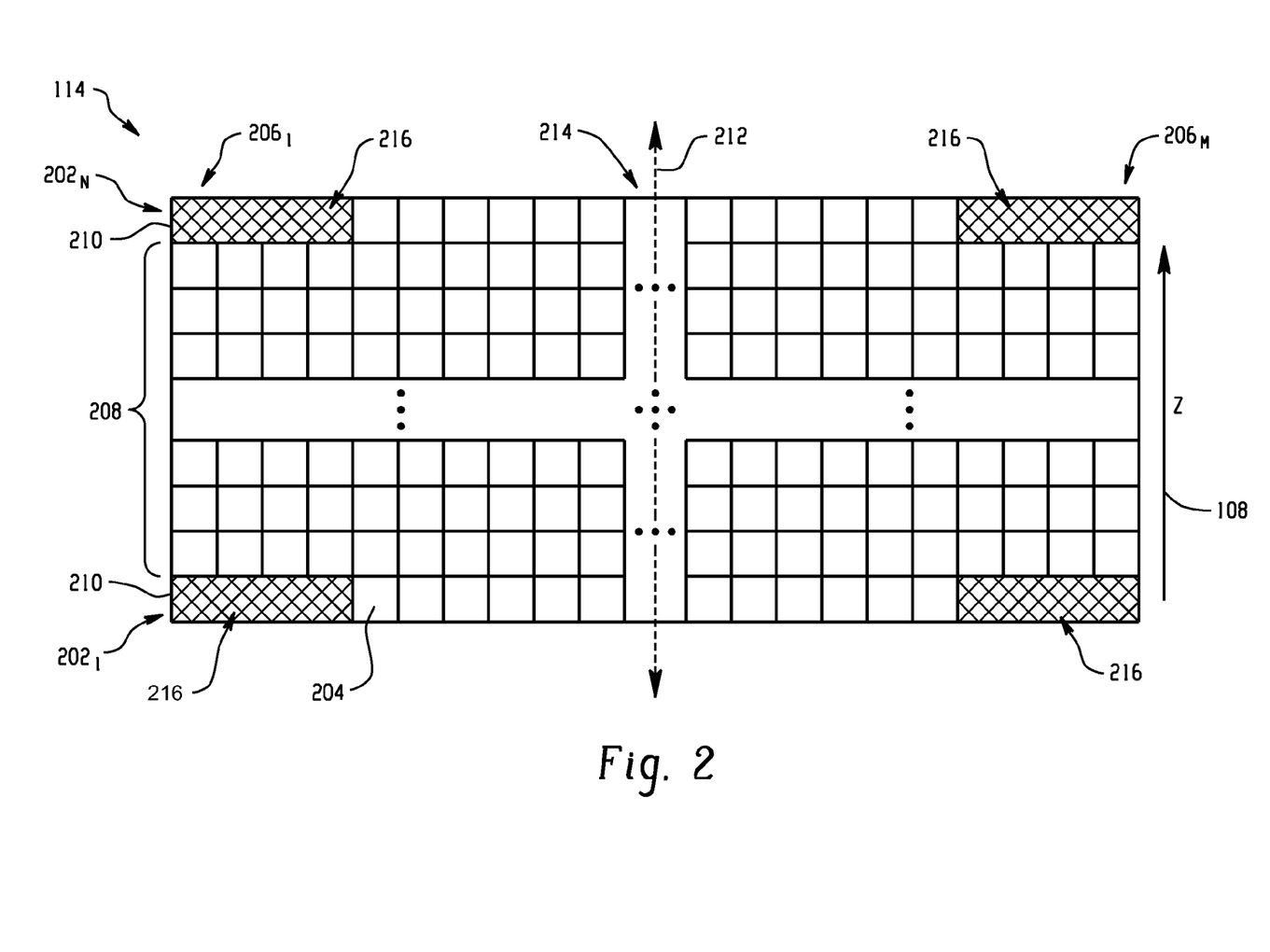
FIG. 2 illustrates an example truncated detector array.

Briefly turning to FIG. 2, the illustrated detector array 114 includes N rows $202_1, \ldots, 202_N$ (e.g., N=16, 64, 320, etc.) of detector modules 204 that extend in the x-y plane and that are arranged with respect to each other along the z-axis 108, forming M columns $206_1, \ldots, 206_M$ of detector modules 204. Each of the detector modules 204 includes a matrix of rows and columns of detector pixels (e.g., 16×16, etc.).

The detector array 114 illustrated in FIG. 2 includes N−2 full (or non-truncated) rows 208 of detector modules 204 and two (2) truncated rows 210 of detectors modules 204. The two truncated rows 210 of detector modules 204 are the two outer most rows $202_1$ and $202_N$ of the detector array 114. A full row 208 of detector modules 204 includes a set of detector modules 204 that extend in the transverse or x-y plane to cover a predetermined patient support, and a truncated row 210 of detector modules 204 includes less detector modules 204.

In the illustrated embodiment, the full rows 208 of detector modules 204 include M detector modules 204, and the truncated rows 210 of detector modules 204 include L detector modules 204, where L<M. For illustrative purposes, L=M−8, and the detector modules 204 in each of the N rows are arranged symmetrically with respect to an imaginary axis 212 extending in the z-axis 108 direction, along a center region 214 of the detector array 114. As such, in the illustrated embodiment the detector array 114 does not include detector modules 204 in corner regions 216.

In other embodiments, there may be more or less truncated rows 210 of detector modules 204, for example, from one (1) truncated row 210 of detector modules 204 up to N−1 truncated rows 210 of detector modules 204. It is to be appreciated that the cost of a truncated detector array 114 (which has a reduced number of detector modules) is likely to be less than that of a non-truncated detector array 114 (with a full set of detector modules 204). In another instance embodiment, the detector modules 204 of at least one of the rows are arranged asymmetrically about the imaginary line 212.

An example of a detector array with a plurality of rows of detector modules, including a central row of detector modules that extends a greater distance (e.g., a greater number of detector modules) in the x-y plane relative to other rows of detector modules is described in U.S. Pat. No. 6,041,097, application Ser. No. 09/055,607, filed Apr. 6, 1998, and entitled "Method and Apparatus for Acquiring Volumetric Image Data using a Flat Panel Matrix Image Receptor," the entirety of which is incorporated herein by reference.

Returning to FIG. 1, a patient support 116, such as a couch, supports an object or subject in the examination region 106.

A general-purpose computing system serves as an operator console 118. Software resident on the console 118 allows the operator to control operation of the system 100 by selecting an imaging protocol that utilizes a reconstruction algorithm that employs project data height rebinning, starting scanning, etc.

Figure 3A:
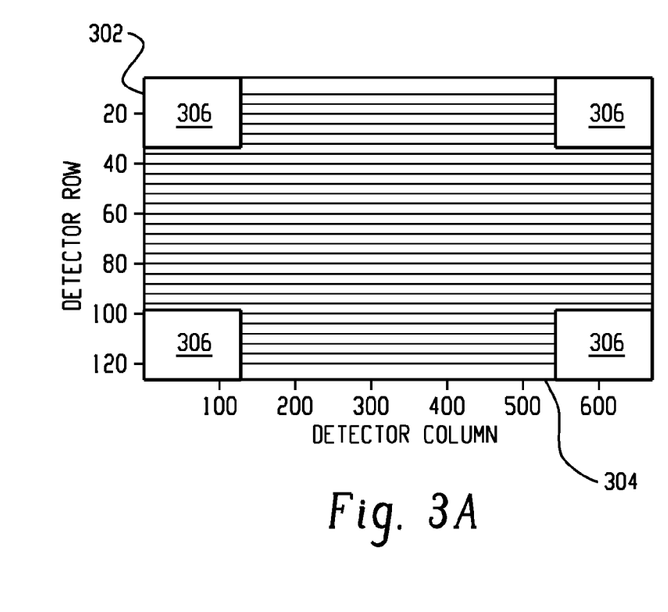
FIGS. 3A and 3B illustrate example projection data generated by the truncated detector array.
Figure 3B:
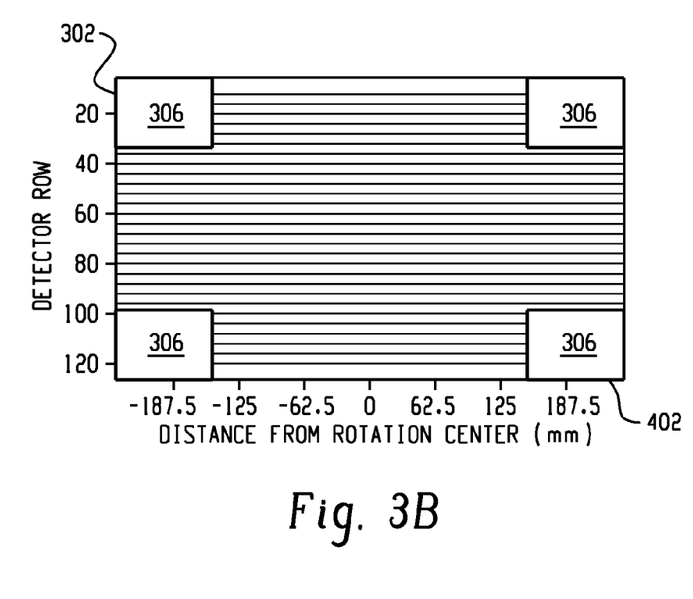

The illustrated embodiment includes a fan-to-parallel beam rebinner 120 that re-bins fan beam projection data generated by the detector array 114 and create parallel beam projection data therefrom. After rebinning, the projections include data that form a parallel and equidistant footprint on the transverse plane. An example of the re-binned projections is illustrated in FIGS. 3A and 3B, which shows a plurality of parallel horizontal projection lines extending along the transverse plane. Note that the projection data is discrete data but is depicted in FIGS. 3A and 3B as continuous data for sake of explanation.

FIG. 3A shows rows of parallel projections (along axis 302) as a function of detector column (axis 304), and FIG. 3B shows the rows of parallel projections (axis 302) as a function of the distance from the rotation center (axis 402). Note that curved in corner regions 306 do not include projection data generated by the detector array 114 and correspond to the corner regions 216 (FIG. 2) of the truncated rows 210 of detectors that do not include any detector modules 204.

In configurations in which the system 100 reconstructs fan beam projection data, the fan-to-parallel rebinner 120 can be omitted. Other suitable processing of the projection data includes, but is not limited to, flying focal spot interleaving, radial re-binning, etc.

Returning to FIG. 1, the projection data generator 122 selectively performs a column-by-column, one dimensional (1D) height (or z-axis) re-binning of the projection data for columns that are close to the corner regions 306 (FIGS. 3A and 3B). By way of example, if the longitudinal beam opening is wide enough to cover the corner regions 306, this height re-binning is performed. Otherwise, it is not performed.

Figure 4A:
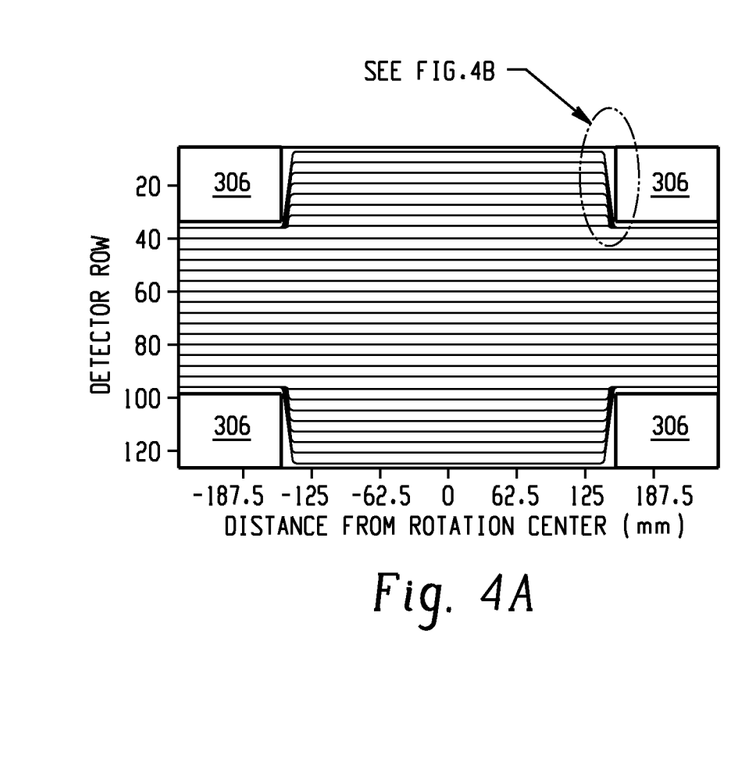
FIGS. 4A and 4B illustrate example projection data after height rebinning.
Figure 4B:
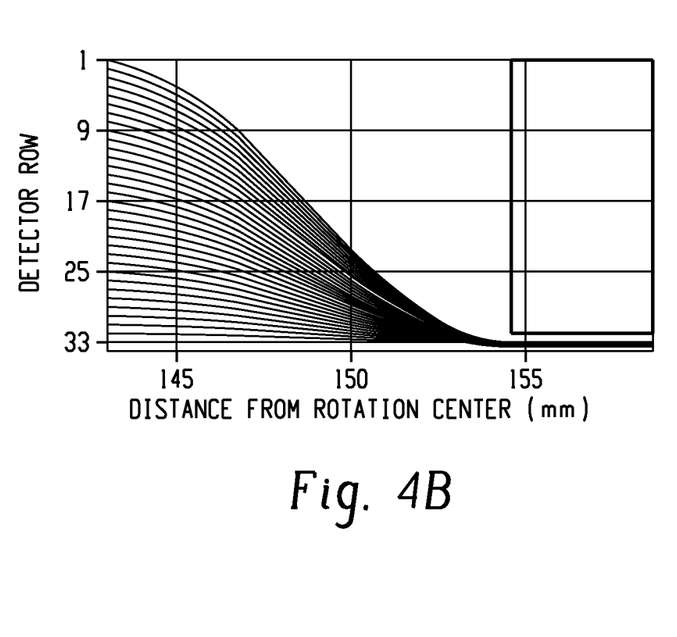

FIG. 4 shows the projection data after height re-binning near the corner regions 306. Note that the augmented projection data now includes quasi-continuous bent lines of readings, which are flat at an inner region and bent or curved at curvature regions, neighbor to the truncated regions. Also note that end regions of the curved lines coincide with end regions of projection data from non-truncated row 208 of detector modules 204.

Returning to FIG. 1, a convolver 124 convolves the augmented projection data (the original set of truncated projection data plus the newly generated projection data) with a ramp or other filter. The convolver 124 convolves the rows of projection data along the straight horizontal projection lines and along the curved projection lines. Without height re-binning, the convolver 124 would convolve default (e.g., zeroes) or arbitrary data representing in the corner regions 306, which may lead to image truncation artifacts.

A back-projector 126 reconstructs the augmented projection data and generates volumetric image data indicative thereof. The illustrated back-projector 126 employs a filtered back-projector algorithm. Where the fan-to-parallel rebinner 120 rebins the fan beam projection data, a parallel beam filter back-projection algorithm is employed, and where the fan-to-parallel rebinner 120 is not used or is omitted from the system 100, a fan beam filter back-projection algorithm is employed.

In one instance, the combination of the projection data generator 122, the convolver 124 and the back-projector 126 are part of a reconstruction system 128. The fan-to-parallel beam rebinner 120 may also be part of the reconstruction system 128. Such a reconstruction 128 can be part of the system 100, as illustrated, or separate therefrom, including located remote from the system 100.

The following describes a non-limiting example of a one dimensional (1D) height rebinning near one of the corner regions 306. Height-rebinning near one or more of the other corner regions 306 can be similarly done.

For this example, the height rebinning is defined according to fractional longitudinal indices of the interpolated projection data and the interpolation algorithm (e.g., nearest neighbor, linear, polynomial, spline, etc.), with the curvature of the projection data being dictated by the fractional indices. In this example, the indices are computed based on EQUATION 1:

$$\begin{cases} m_i = D_T - (RT+1) \cdot T_T + 1; \\ m_o = D_T - RT \cdot T_T. \end{cases} \quad \text{EQUATION 1}$$

where $m_i$ is the index for the most inner detector column of the curved region 306 (FIGS. 3A and 3B), $m_o$ is the index for the most outer detector column of the curved region 306 (FIGS. 3A and 3B1), $D_T$ is the transverse dimension of a non-truncated row of detector modules 204, RT denotes the number of truncated or missing detector modules 204 in the corner region 306, and $T_T$ denotes the number of pixels in a detector module 204 in the transverse direction.

The fractional longitudinal indices can be determined based on Equation 2:

$$FLI(n \in [1:T_l], r \in [r(m_i)r(m_o)]) = \qquad \text{EQUATON 2}$$
$$n \cdot \cos\left(\frac{\pi}{2} \cdot \frac{r - r(m_i)}{r(m_o) - r(m_i)}\right)^2 +$$
$$(T_L + 1) \cdot \sin\left(\frac{\pi}{2} \cdot \frac{r - r(m_i)}{r(m_o) - r(m_i)}\right)^2.$$

where FLI is the fractional longitudinal indices, r denotes the radial distance between a transversally re-binned projection and the rotation axis, and $T_L$ denotes the number of pixels in a detector module 204 in the longitudinal direction. For each detector column, $T_L$ projections are interpolated into $T_L$ readings.

As explained in greater details below, the convolved readings belonging to the curved lines are extrapolated in some instances to cover fully, or partially, the regions of missing modules in the corner regions 306.

For helical scans with a transversal reconstructed field of view (FOV) that is off-centered with respect to the gantry rotation axis, the generalized diameter that determines the maximal pitch allowed is the largest distance between any of the reconstructed pixels and the rotation axis multiplied by two. Using a three-dimensional (3D) back-projection, the maximal allowed pitch dependence on the FOV diameter is determined by letting each of the reconstructed pixels be illuminated by an angular range of projections that equals at least to $\pi+\delta$, where $\delta$ is a small and finite angle that suppresses motion artifacts.

As long as the FOV diameter is less than $2 \cdot r(m_i)$, the maximal pitch allowed for the truncated detector array 114 (FIG. 1) is about equal to that allowed for a full (non-truncated) detector array. However, when the FOV diameter is greater than $2 \cdot r(m_i)$, the maximal pitch for the truncated detector array 114 (FIGS. 1 and 2) is reduced as shown in EQUATION 3:

$$p_{max}^{new} = p_{max}^{conventional} \cdot (1 - 2 \cdot T_l/D_l) \qquad \text{EQUATION 3}$$

where $p_{max}^{new}$ is the maximum pitch factor for the truncated detector array 114 (FIG. 2), $p_{max}^{conventional}$ is the maximum pitch factor for a non-truncated detector array, $T_l$ is the longitudinal distance (in pixels) of a detector module 204, and $D_l$ is the number of detector modules extending in the longitudinal direction (or the number of rows of detector modules). Based on EQUATION 3, for $T_l=16$ and $D_l=128$, the maximal pitch of the truncated detector array 114 (FIG. 1) would be reduced by 25% relative to the maximum pitch of a non-truncated detector array.

One approach to overcoming this reduction in pitch factor, partially or completely, is to create data for at least a sub-portion of the corner regions 306 (FIGS. 3A and 3B) via extrapolation of the convolved readings belonging to the bent. By using a Frequency Split reconstruction technique, artifacts near strong z-gradients of the patient CT map due to the extrapolated data and/or to the strong curvature of the projection data generated by the projection data generator 122 (FIG. 1) can be mitigated. A suitable Frequency Split reconstruction is described in "The frequency split method for helical cone-beam reconstruction," G. Shechter, T. Koehler, A. Altman and R. Proksa, Medical Physics, Vol. 31, No. 8, pp. 2230-2236, August 2004.

With the above-noted Frequency Split reconstruction, the low-frequency components and the high-frequency components of the projection data within the transverse plane are reconstructed separately. Cone beam artifacts, artifacts that might arise due to the strong curvature of the projection data, and artifacts due to the longitudinal extrapolation generally result from low transversal frequencies. As such, the back-projection 126 (FIG. 1) reconstructs the low frequency components by assigning finite back-projection weights only to readings of inner detector rows that are free of curvature and extrapolation. The back-projection 126 (FIG. 1) reconstructs the high frequency components by taking into account all of the detector rows for reducing noise does not increase the level of image artifacts.

For axial (or circular) scans, the generalized transverse FOV diameter used for helical scans (discussed above) is replaced with r(v), which gives the transverse distance between the pixel v and the rotation axis.

H represents the longitudinal distance between a reconstructed pixel and the z-coordinate of the tube. The dependence of the maximal value for H that allows reconstructing the pixel on r(v) decreases monotonically. To obtain this dependence for the full (non-truncated) detector array for a pixel v, an angle $\theta \in [0, \pi)$ describes the transversal canonical orientation of a reading to be back-projected to the pixel.

Using a three-dimensional back-projection within an approximate reconstruction algorithm based on a 2D Fourier decomposition, a pixel can be reconstructed as long as it is illuminated by at least one of the two transversally re-binned conjugate projections that includes readings with an angle $\theta$. For a full (non-truncated) detector array, the dependence of the maximal value for H is on r(v) as shown in EQUATION 4:

$$H_W(r(v)) = \frac{\Sigma}{2} \cdot \sqrt{1 - \frac{r(v)^2}{SID^2}} \qquad \text{EQUATION 4}$$

where SID is the tube trajectory radius, and $\Sigma$ is the longitudinal beam opening projected to the rotation axis.

In some instances, the pixel must be covered by the geometrical illumination window of both conjugate projections having the canonical angle $\theta \in [0, \pi)$. Examples of two such instances include phase selective one hundred and eighty degree (180°) back-projection, and three-hundred and sixty degree (360°) back-projection when back-projecting the two conjugate projections into the pixel to reduce the level of cone beam artifacts. For these cases, the dependence of the maximal value for H is shown in EQUATION 5:

$$H_N(r(v)) = \frac{\Sigma}{2} \cdot \left(1 - \frac{r(v)}{SID}\right). \qquad \text{EQUATION 5}$$

Where $H_W > H_N$, EQUATION 4 offers wider coverage that might be of importance for perfusion applications. In order to not reduce the coverage with the truncated detector array 114, the values for $H_W$ and $H_N$ for the truncated detector array 114 should be the same or substantially similar to those for the non-truncated detector array. For this, a longitudinal extrapolation of the convolved readings of the outer curved filter lines, similar to that performed for the helical scan, is performed, when necessary.

Figure 5:
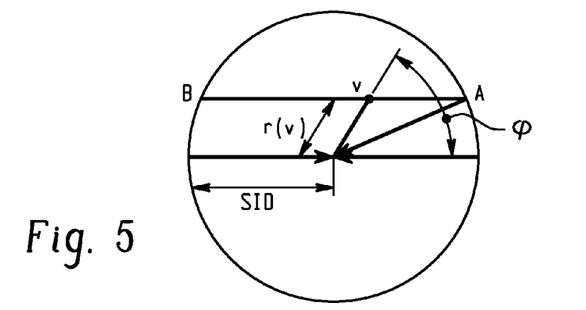
FIG. 5 illustrates a transversal footprint of a pixel.

The extent of the extrapolation is discussed in connection with FIG. 5, which shows the transversal footprints of a pixel v and the projection readings oriented without loss of generality from right to left. The angle $\phi$ denotes the pixel polar angle with respect to the projection.

For the transverse footprint $\overline{AB}$, which corresponds to the reading with the maximal cone angle out of the readings of the projection that intersect the pixel in the 2D sense, the z-coordinate of the point on this reading, which has a transverse footprint identical to that of the pixel v for the full non-truncated detector array, can be defined based on EQUATION 6:

$$z_{max}^{conventional} = \frac{\Sigma}{2} \cdot \cos(a\sin(r(v)\sin(\varphi)/SID) - r(v) \cdot \cos(\varphi)/SID).$$ EQUATION 6

The corresponding coordinate for the truncated detector array 114 can be defined based on EQUATION 7:

$$z_{max}^{new} = z_{max}^{conventional} \cdot \begin{cases} r(v) \cdot abs(\sin(\varphi)) \le r(m_i) & 1 \\ r(m_i) < r(v) \cdot abs(\sin(\varphi)) < r(m_o) & FLI(1, r(v) \cdot 1 - \frac{abs(\sin(\varphi)) - 1}{D_L/2} \\ r(m_o) \le r(v) \cdot abs(\sin(\varphi)) & T_L/(D_L/2) \end{cases}$$ EQUATION 7

The maximal extrapolation extent can be determined as the difference between the pixel's z-coordinate and $z_{max}^{new}$, as shown in EQUATION 8:

$$\Delta z_{ext} = \max(H_{W(N)} - z_{max}^{new}, 0).$$ EQUATION 8

Once $\Delta z_{ext}$ is set for a given pixel v and for the two conjugate projections that share the same angle $\theta \in [0,\pi)$, the back-projection weighting, of the two readings interpolated from these two projections and back-projected to the pixel, depends now not only on their cone angles denoted by $\beta^{1,2}(v,\theta)$, but also on $\Delta z^{1,2}(v,\theta)$, wherein the superscript index stands for the direct and the conjugate projection. The back-projection weighting is based on EQUATION 9, which is a generalized conventional aperture weighted back-projection:

$$W^{1,2}(v,\theta) = W^{1,2}(\beta^{1,2}(v,\theta), \Delta z^{1,2}(v,\theta)).$$ EQUATION 9

EQUATIONS 10, 11, and 12 provide a non-limiting example of this weighting.

$$W^{1,2}(\beta^{1,2}(v,\theta), \Delta z^{1,2}(v,\theta)) = \frac{w^{1,2}(\beta^{1,2}(v,\theta), \Delta z^{1,2}(v,\theta))}{\sum_{i=1}^{2} w^i(\beta^i(v,\theta), \Delta z^i(v,\theta))},$$ EQUATION 10

$$w(\beta, \Delta z) = w_{conventional}(\beta) \cdot w_{new}(\Delta z), \text{ and}$$ EQUATION 11

$$w_{new}(\Delta z) = 1 - \min\left(\frac{\Delta z}{\Delta z_m}, 1\right)$$ EQUATION 12 where $\Delta z_M$ is the maximal extrapolation extent necessary to reconstruct all the pixels, and $w_{conventional}$ is the conventional cone angle dependent non-normalized aperture weight. Note that in this example, for $\Delta z^{1,2}(v,\theta)=0$ conventional aperture weighting is used.

Note that EQUATION 9 is valid for the 360° mode, as well as for the gated or non-gated 180° modes. For 360° and cardiac 180° back-projection, with $H \le H_N$ the amount of z-extrapolation is small. For example, using SID=570 mm, $\Sigma$=80 mm, $D_L$=128, $T_L$=16, RT=8, and $D_T$=128, assuming a symmetric detector array with respect to the rotation axis, and letting the curvature regions of the projection lines extend over three modules, the maximal extrapolation amount is zero for $r(v) \le 150$. In other words, no extrapolation is required for the cardiac FOV of 250 mm. The maximal extrapolation for all of the angles $\varphi$ increases monotonically with higher values of $r(v)$ and is about 4 mm for $r(v)$=250. Since the back-projection weight of a reading obtained with a larger extrapolation than that of a conjugate reading that intersects the voxel is smaller than that of the conjugate reading, the impact of the extrapolation required for the 360° back-projection at large $r(v)$ can be ignored.

For the wide coverage back-projection with $H \le H_W$, the extrapolation is negligible within the cardiac FOV. At larger $r(v)$, the extrapolation from both conjugate readings increases at specific $\varphi$ angles and $H \approx H_W$ to about 9 mm. Using the full (non-truncated) detector array to reconstruct pixels with a longitudinal offset $H \approx H_W$ is not well-suited in the sense that unacceptable cone beam artifacts might arise, especially for narrow reconstructed slice widths. Using the high-frequency longitudinal nature of the cone beam artifacts, this ill-posed problem of the wide coverage mode can be reduced, although only to some extent, by using wide reconstructed slice widths such as 5 mm. In this case, the impact of the longitudinal extrapolation that is limited for specific $\varphi$ angles should also not deteriorate the clinical diagnosis.

Figure 6A:
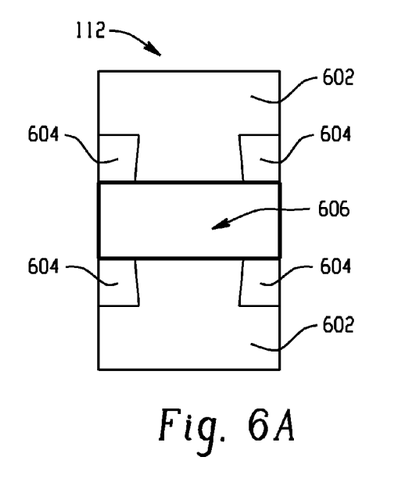
FIGS. 6A, 6B, and 7 illustrate an example collimator for the truncated detector array.
Figure 6B:
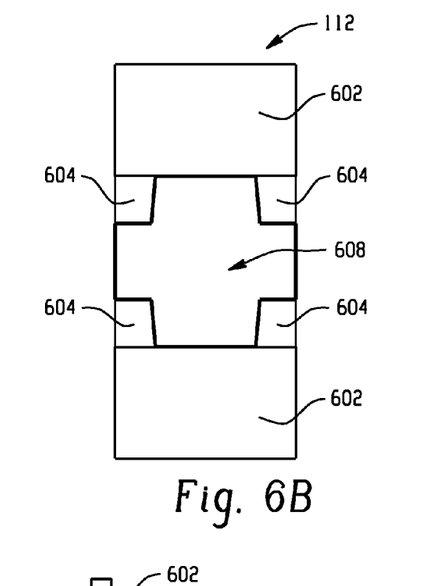
Figure 7:
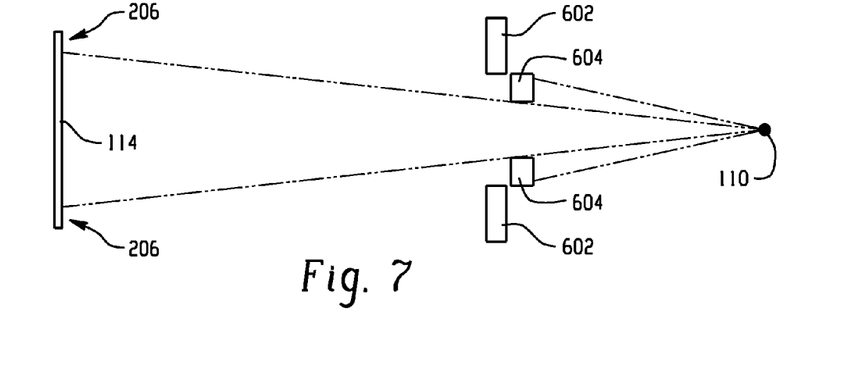

As noted above in connection with the description of FIG. 1, in one instance, the source collimator 112 (FIG. 1) includes a set of dynamic collimators that selectively define a longitudinal beam opening (LBO) and a set of static collimators that attenuate radiation regardless of the LBO. FIGS. 6A, 6B and 7 illustrate an example of such a collimator.

Initially referring to FIGS. 6A and 6B, the collimator 112 includes a set of dynamic collimators 602 and a set of static collimators 604. The set of static collimators 604 are located in the path between the radiation source 110 (FIG. 1) and the truncated corner regions 216 (FIG. 2) of the truncated detector array 114 (FIG. 2). The set of dynamic collimators 602 are configured to move in coordination to define at least two LBOs, LBO 606 (FIG. 6A) and LBO 608 (FIG. 6B).

When the set of dynamic collimators 602 define LBO 606 (FIG. 6A), the transversal beam opening is the same or substantially similar to that for a non-truncated detector array, and the static collimators 604 do not block any of the radiation that traverses through the dynamic collimators. When the set of dynamic collimators 602 define the LBO 608 (FIG. 6B), the LBO includes the corner regions 216 (FIG. 2) without the detector modules of the truncated detector array 114 and the set of static collimators 604 block radiation that would otherwise illuminate the corner regions 216 (FIG. 2) and that would not contribute to the reconstructed images.

The above allows for mitigating truncation artifacts and maintaining high dose utility and reducing patient dose relative to a configuration in which the set of static collimators 604 are omitted. FIG. 7 illustrates the dynamic and static collimators 602 and 604 from a side view.

Figure 8:
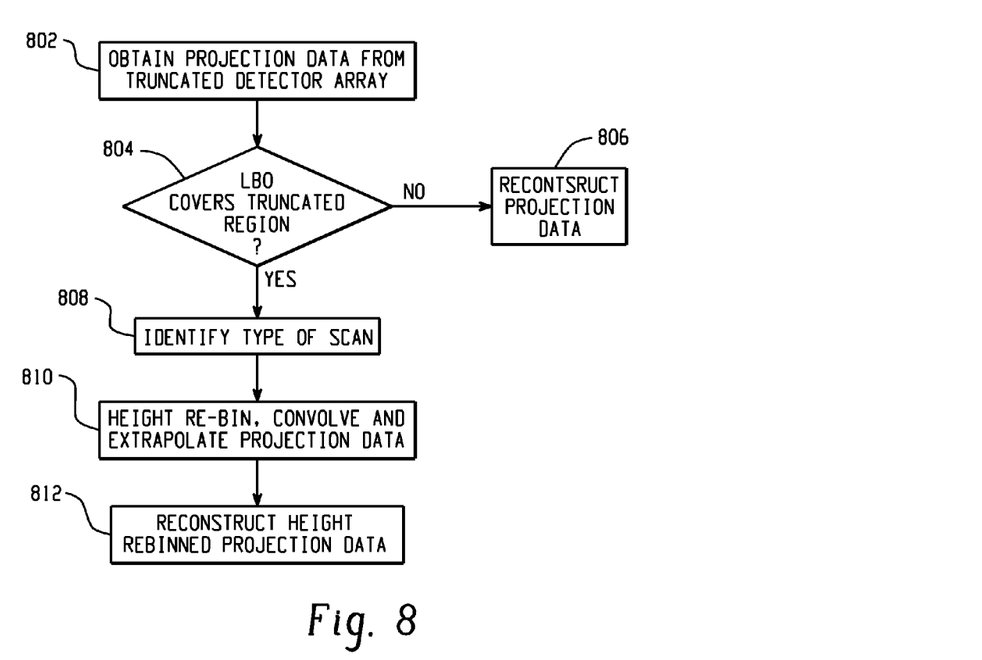
FIGS. 8 and 9 illustrate example methods.

FIG. 8 illustrates a method for processing projection data generated with the truncated detector array 114 (FIGS. 1 and 2).

At 802, obtain projection data generated with the truncated detector array 114.

At 804, determine if the LBO includes at least a sub-portion of the truncated region of the detector array 114.

At 806, if not, then reconstruct the projection data.

Otherwise, at 808, identify the scan type as either helical or axial.

At 810, height re-bin, convolve, and extrapolate at least a portion of the projection data to generate projection data for region of the truncated region covered by the LBO based on the type of scan.

At 812, reconstruct the height rebinned projection data.

Figure 9:
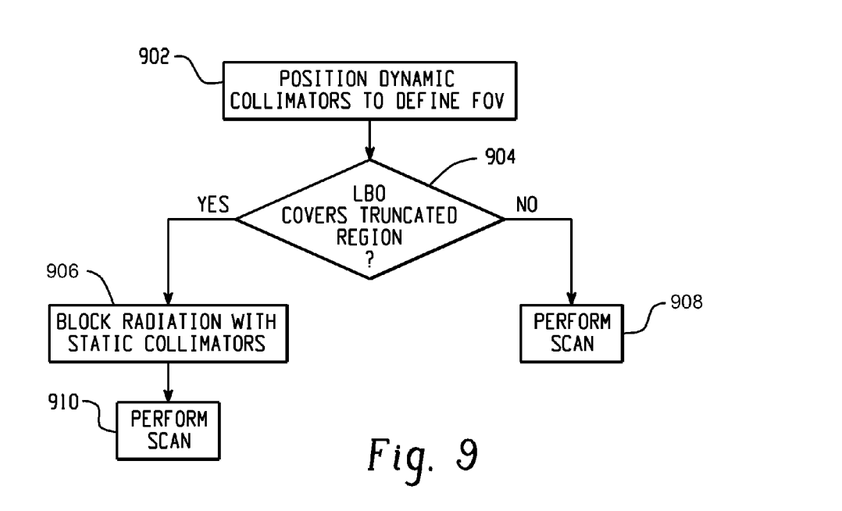

FIG. 9 illustrates a method for scanning using a truncated detector array 114 (FIGS. 1 and 2).

At 902, position a set of dynamic collimators 602 to define a LBO.

At 904, if the LBO does not cover at least a sub-portion of the truncated region of the detector array 114, then perform the scan. The resulting projection data can be reconstructed to generate volumetric image data and one or more images based thereon.

At 906, if the LBO covers at least a sub-portion of the truncated region of the detector array 114, then block via a set of static collimators 604 the radiation that would illuminate the truncated region, and at 908, the scan is performed. The resulting projection data can be height rebinned and reconstructed to generate volumetric image data and one or more images based thereon.

The above can be implemented as a console application of a scanner and/or an image processing or planning workstation. By way of example, the above may be implemented by way of computer readable instructions, which when executed by a computer processor(s) (a processor of the console or workstation), cause the processor(s) to carry out the described acts. The instructions are stored in a computer readable storage medium associated with or otherwise accessible to the relevant computer.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A reconstruction system that reconstructs projection data generated by a detector array of an imaging system having at least one truncated row of detector modules, comprising:
   a projection data generator that augments the projection data with projection data created for the at least one truncated row of detector modules;
   a convolver that convolves the augmented projection data; and
   a back-projector back-projects the augmented projection data and generates volumetric image data indicative thereof.

2. The system of claim 1, wherein the detector array includes two outer rows of detector modules and at least one inner row of detector modules, located between the two outer rows, wherein at least one of the two outer rows of detector modules is the at least one truncated row.

3. The system of claim 1, wherein the projection data generator longitudinally interpolates projection data for the at least one truncated row.

4. The system of claim 3, wherein the interpolation generates quasi-continuous bent lines of projection data with a flat inner region and bent outer regions that correspond to truncated regions of the detector array.

5. The system of claim 4, wherein bent regions coincide with end regions of projection lines that correspond to non-truncated rows of detector modules.

6. The system of claim 5, wherein the convolver convolves the augmented projection data with a filter along the flat regions and along bent regions.

7. The system of claim 1, wherein the filtered projection data is extrapolated longitudinally at outer transverse regions of the truncated row.

8. The system of claim 7, wherein the longitudinal extrapolation creates an amount of data for reconstruction that equals a same volumetric region of interest reconstructed with a non-truncated detector array.

9. The system of claim 7, where the amount of extrapolation is determined differently for different scan modes, including a helical scan mode, a circular scan with a 360° reconstruction scan mode, a gated circular scan with 180° reconstruction scan mode, and a non-gated circular scans with 180° reconstruction scan mode.

10. The system of claim 1, wherein, for helical scans, projections of high and low transversal frequencies are convolved and back-projected separately along projections.

11. The system of claim 1, wherein, for axial scans, the back-projector employs one of a 360° back-projection algorithm and cardiac or non-cardiac 180° reconstruction algorithm.

12. The system of claim 1, wherein the back-projector employs a weighted back-projection algorithm that takes into account cone angles of conjugate readings that intersect a pixel and a longitudinal distance to extrapolate each of the readings.

13. The system of claim 1, wherein the imaging system includes a source collimator having a dynamic portion that defines a longitudinal beam opening and a static portion that blocks radiation that would otherwise illuminate a portion of the at least one truncated row that does not include a detector module.

14. A method, comprising: reconstructing wide-coverage cone-beam CT projection data generated by a detector array of an imaging system, wherein the detector array includes at least one truncated outer row of detector modules and at least one non-truncated inner row of detector modules.

15. The method of claim 14, further comprising:
   longitudinally interpolating outer projection data of the at least one truncated outer row;
   convolving the interpolated projection data line-by-line; and
   longitudinally extrapolating the convolved projection data near the outer transverse regions.

16. The method of claim 15, wherein projections of high and low transversal frequencies are filtered and back-projected separately using a Frequency Split technique.

17. The method of claim 15, wherein the imaging system includes a source collimator having a dynamic portion that defines a longitudinal beam opening and a static portion that blocks radiation that would otherwise illuminate a portion of the at least one truncated row that does not include a detector module.

18. An imaging system, comprising:
   a radiation source that rotates around and emits radiation that traverses an examination region;
   a two dimensional truncated detector array having at least one truncated outer row of detector modules with an outer end region that does not include a detector module, wherein the detector array generates projection data indicative of the radiation traversing the examination region; and
   a radiation source collimator, including:
      a set of dynamic collimators; and
      a set of static collimators.

19. The imaging system of claim 18, wherein the set of dynamic collimators are configured to define at least two different longitudinal beam openings and one of the longitudinal beam openings does not cover one or more outer end regions that do not include a detector module.

20. The imaging system of claim 19, wherein the two dimensional truncated detector array includes at least one inner row of detector modules, located between two outer rows, and the at least one inner row of detector modules is a full, non-truncated row of detector modules, wherein a truncated row of detector modules includes less detector modules than the full, non-truncated row of detector modules.

21. The imaging system of claim 19, wherein the other of the longitudinal beam opening covers one or more outer end regions that do not include a detector module.

22. The imaging system of claim 18, wherein the set of static collimators are positioned with respect to the detector array to block radiation emitted by the source that would otherwise illuminate the one or more outer end regions.

23. The imaging system of claim 18, further comprising:
 a projection data generator that augments the generated projection data with projection data for the outer end region that does not include a detector module;
 a convolver that convolves the augmented projection data; and
 a back-projector that back-projects the augmented projection data and generates volumetric image data indicative thereof.

* * * * *